United States Patent
Jonas et al.

(10) Patent No.: US 12,024,557 B2
(45) Date of Patent: Jul. 2, 2024

(54) EGFR BLOCKING AGENTS FOR THE THERAPEUTIC TREATMENT OF MYOPIA

(71) Applicants: Shefali Brinda Jonas, Weinheim (DE); Rahul Arvo Jonas, Weinheim (DE); Jost B. Jonas, Weinheim (DE); Songhomitra Panda-Jonas, Weinheim (DE)

(72) Inventors: Shefali Brinda Jonas, Weinheim (DE); Rahul Arvo Jonas, Weinheim (DE); Jost B. Jonas, Weinheim (DE); Songhomitra Panda-Jonas, Weinheim (DE)

(*) Notice: Subject to any disclaimer, the term of this patent is extended or adjusted under 35 U.S.C. 154(b) by 397 days.

(21) Appl. No.: 17/229,303

(22) Filed: Apr. 13, 2021

(65) Prior Publication Data
US 2021/0340237 A1 Nov. 4, 2021

Related U.S. Application Data

(62) Division of application No. 15/558,139, filed as application No. PCT/EP2016/000460 on Mar. 15, 2016, now Pat. No. 11,008,385.

(30) Foreign Application Priority Data
Mar. 16, 2015 (EP) .................................. 15000771

(51) Int. Cl.
*A61K 38/18* (2006.01)
*A61P 27/10* (2006.01)
(Continued)

(52) U.S. Cl.
CPC .............. *C07K 16/22* (2013.01); *A61P 27/10* (2018.01); *C07K 14/485* (2013.01); *C07K 16/28* (2013.01);
(Continued)

(58) Field of Classification Search
None
See application file for complete search history.

(56) References Cited

U.S. PATENT DOCUMENTS

| 6,204,359 B1 | 3/2001 | Delaey et al. |
| 8,142,782 B2 * | 3/2012 | He .................... A61P 25/00 514/266.4 |

(Continued)

FOREIGN PATENT DOCUMENTS

WO    2004073734 A1    9/2004

OTHER PUBLICATIONS

Dong et al., Blockade of epidermal growth factor and its receptor and axial elongation in experimental myopia, DOI: 10.1096/fj.202001095RR, The FASEB J. 34:13654-13670, 2020.*

(Continued)

*Primary Examiner* — Claire Kaufman
(74) *Attorney, Agent, or Firm* — Viksnins Harris Padys Malen LLP (57) ABSTRACT

The present invention relates to agents for use in the prophylactic or therapeutic treatment of myopia in a subject, wherein said agents are capable of decreasing epidermal growth factor receptor (EGFR) signaling and/or signaling of another receptor susceptible for amphiregulin in a subject in a direct or indirect manner. The present invention further relates to agents for use in the prophylactic or therapeutic treatment of hyperopia in a subject, wherein said agents are capable of increasing epidermal growth factor receptor (EGFR) signaling and/or signaling of another receptor susceptible for amphiregulin in a subject. Furthermore, the present invention relates to methods for the diagnosis of myopia or hyperopia in a subject, comprising the steps of (a) providing a biological sample from the subject; (b) determining the amphiregulin level in said sample; (c) comparing the level determined in step (b) to the amphiregulin levels
(Continued)

found in emmetropic subjects or subjects going to be emmetropic; and (d) determining that the subject has myopia or is predisposed for the development of myopia in case the level determined in step (b) is higher than the amphiregulin levels found in emmetropic subjects or subjects going to be emmetropic; and determining that the subject has hyperopia or is predisposed for the development of hyperopia in case the level determined in step (b) is lower than the amphiregulin levels found in emmetropic subjects or subjects going to be emmetropic. Finally, the present invention relates to a method for identifying agents which associate with amphiregulin or fragments or variants thereof.

3 Claims, 4 Drawing Sheets

Specification includes a Sequence Listing.

(51) Int. Cl.
  C07K 14/485      (2006.01)
  C07K 16/22       (2006.01)
  C07K 16/28       (2006.01)
  G01N 33/68       (2006.01)
(52) U.S. Cl.
  CPC ..... G01N 33/6893 (2013.01); G01N 2333/71 (2013.01); G01N 2500/00 (2013.01); G01N 2800/16 (2013.01)

(56) References Cited

U.S. PATENT DOCUMENTS

| | | | |
|---|---|---|---|
| 8,658,175 B2* | 2/2014 | Dubridge | A61P 35/00 530/387.9 |
| 11,008,385 B2 | 5/2021 | Jonas et al. | |
| 2016/0008480 A1* | 1/2016 | Lee | A61K 47/6851 530/358 |
| 2018/0030098 A1* | 2/2018 | Bosse-Doenecke | A61P 35/00 |

OTHER PUBLICATIONS

Jonas et al., Intraocular epidermal growth factor concentration, axial length, and high axial myopia, doi.org/10.1007/s00417-021-05200-5, Graefes Arch Clin Exp Ophthalmol. 259, 3229-3234, 2021.*
Conidi et al.,Aptamers and Their Potential to Selectively Target Aspects of EGF, Wnt/β-Catenin and TGFB-Smad Family Signaling, doi:10.3390/ijms14046690, Intl. J. Mol. Sci., 14:6690-6719, 2013.*
Peipp et al.,Sensitivity and resistance to EGF-R inhibitors, doi.org/10.4161/mabs.1.6.10051, mAbs, 1:6, 590-599, 2009.*
Bikbov et al., Intravitreal panitumumab and myopic macular degeneration, doi: 10.1136/bjo-2023-323383, Brit. J. Ophthalmol. Jul. 10, 2023.*
Boersrma et al., Bispecific Designed Ankyrin Repeat Proteins (DARPins) Targeting Epidermal Growth Factor Receptor Inhibit A431 Cell Proliferation and Receptor Recycling, J. Blol. Chem. 286(48): 41273-41285, Dec. 2, 2011.*
Mintz et al., Protein Scaffolds, Bioprocess Intl. Retrieved onine from <URL:https://bioprocessintl.com/upstream-processing/expression-platforms/protein-scaffolds-339588/> [retrieved on Sep. 5, 2023], 13 pages, Feb. 2, 2013.*
Ho et al., The ophthalmological complications of targeted agents in cancer therapy_ what do we need to know as ophthalmologists, Acta Ophthalmol. 91:604-609, 2012.*
Upadhyay et al., Biological Mechanisms of Atropine Control of Myopia, Eye Contact Lens;46: 129-135, 2020.*
Berasain, C , et al., "Amphiregulin", Seminars in Cell & Developmental Biology 28, 31-41 (2014).
Berasain, C , et al., "Novel Role for Amphiregulin in Protection from Liver Injury", Journal of Biological Chemistry 280(19), 19012-19020 (2005).
Bhardwaj, V , et al., "Axial Length, Anterior Chamber Depth—A Study in Different Age Groups and Refractive Errors" Journal of Clinical and Diagnostic Research 7(10), 2211-2212 (2013).
Cheng, C , et al., "Nine Loci for Ocular Axial Length Identified through Genome-wide Association Studies, Including shared Loci with Refractive Error", The American Journal of Human Genetics 93, 264-277 (2013).
Dong, L , et al., "Amphiregulin and ocular axial length", Acta Ophthalmol 97, e460-e470 (2019).
European Patent Office , Response to Communication pursuant to Rules 161(1) and 162 EPC for EP Application No. 16720043.5, 22 pages, Apr. 30, 2018.
Fang, Y , et al., "Progression of Myopic Maculopathy during 18-Year Follow-up", Ophthalmology doi.org/10.1016/j.ophtha.2017.12.005, ISSN 0161-6420/17, 15 pages (2017).
Fassler, J , et al., "BLAST Glossary", in BLAST Help, Natl. Lib. Med., Retrieved online: <URL:https://www.ncbi.nlm.nih.gov/books/NBK62051/.>, [Retrieved on Aug. 3, 2020], Jul. 14, 2011.
Gephart, J , "The Trafficking of Amphiregulin in Polarized Epithelial Cells", Dissertation submitted to Faculty of Graduate School of Vanderbilt University, for degree of Doctor of Philosophy in Cell and Developmental Biology, 190 pages (Aug. 2011).
Gu, X , et al., "Age-Related Changes in the Retinal Pigment Epithelium (RPE)", PLoS One 7(6), 38673, 13 pages (2012).
Harvard Men's Health Watch , "Growth hormone, athletic performance, and aging", Retrieved online: <URL:https://www.health.harvard.edu/diseases-and-conditions/growth-hormone-athletic-performance-and-aging>, [Retrieved on Aug. 4, 2020], Jun. 19, 2018.
Jiang, W , et al., "Amphiregulin Antibody and Reduction of Axial Elongation in Experimental Myopia", EBioMedicine 17, 134-144 (2017).
Jonas, J , et al., "Exhibit 1", Submitted to European Patent Office (EPO) in Response filed Apr. 30, 2018 for EP Application No. 16720043.5.
Jonas, J , et al., "Exhibit 2", Submitted to European Patent Office (EPO) in Response filed Apr. 30, 2018 for EP Application No. 16720043.5.
Jonas, J , et al., "Exhibit 3", Submitted to European Patent Office (EPO) in Response filed Apr. 18, 2019 for EP Application No. 16720043.5.
Jonas , et al., "Exhibit 4", Submitted to European Patent Office (EPO) as Exhibit 6 in Submission filed Sep. 17, 2020 for EP Application No. 16720043.5.
Kawasaki, S , et al., "Up-regulated gene expression in the conjuctival epithelium o fpatients with Sjogren's syndrome", Experimental Eye Research 77, 17-26 (2003).
Lee, J , et al., "Progression and Longitudinal Biometric Changes in Highly Myopic Eyes", IOVS 61(4), Article 34, 7 pages (2020).
Liu, B , et al., "Epidermal Growth Factor Receptor Activation: An Upstream Signal for Transition of Quiescent Astrocytes into Reactive Astrocytes after Neural Injury", Journal of Neuroscience 26(28), 7532-7540 (2006).
McGovern, M , et al., "Reye's syndrome and aspirin: lest we forget", BMJ 322, 1591-1592 (2001).
Patent Cooperation Treaty , International Searching Authority, Search Report and Written Opinion for PCT/EP2016/000460, 15 pages, Jul. 8, 2016.
Peterson, J , et al., "The Role of Endogenous Epidermal Growth Factor Receptor Ligands in Mediating Corneal Epithelial Homeostasis", Invest Ophthalmol Vis Sci 55, 2870-2880 (2014).
Radhika, M , et al., "Pharmacokinetics of intravitreal antibiotics in endophthalmitis", Journal of Ophthalmic Inflammation and Infection 4(22), 9 pages (2014).
Simpson, C , et al., "Genome-Wide Meta-Analysis of Myopia and Hyperopia Provides Evidence for Replication of 11 Loci", PLoS One 9(9), e107110, 19 pages (2014).
Verhoeven, V , et al., "What causes myopia?: Complex genetics and epidemiology of a common condition", Thesis (2015), retrieved from the internet: URL:http://www.google.de/url?sa=t&rct=j&q=

(56) References Cited

OTHER PUBLICATIONS

&esrc=s&source=web&cd=I&ved=OahUKEwiWncuE3 8 NAhVKJpoKHWyBBaMQFggeMAA&urI=http%3A%2F%2Frepub. eur.nl%2Fpub%2F78245%2FI50616 Verh oeven-Virginie-Johanna- . . . .

Wakazono, T, et al., "Time-Course Change in Eye Shape and Development of Staphyloma in Highly Myopic Eyes", Invest Ophthalmol Vis Sci 59, 5455-5461 (2018).

Wang, X, et al., "Gene Expression Changes under Cyclilc Mechanical Stretching in Rat Retinal Glial (Muller) Cells", PLOS One 8(5), e63467, 10 pages (2013).

Wang, D, et al., "Longitudinal Changes of Axial Length and Height Are Associated and Concomitant in Children", Invest Ophthalmol Vis Sci 52, 7949-7953 (2011).

Xiao, X, et al., "Therapeutic Effects of Epidermal Growth Factor on Benzalkonium Chloride—Induced Dry Eye in a Mouse Model", Investigative Ophthalmology & Visual Science 53(1), 191-197 (2012).

Yanagihara, R, et al., "Pseudophakic adult with progressive optic disc tilt and axial length elongation", American Journal of Ophthalmology Case Reports 19, 100814, 3 pages (2020).

\* cited by examiner

SEQUENCE LISTING

<160> NUMBER OF SEQ ID NOS: 3

<210> SEQ ID NO 1
<211> LENGTH: 252
<212> TYPE: PRT
<213> ORGANISM: Homo sapiens

<400> SEQUENCE: 1

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
            115                 120                 125

Lys Gly Gly Lys Asn Gly Lys Asn Arg Arg Asn Arg Lys Lys Lys Asn
        130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
    210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA antisense strand targeting human amphiregulin mRNA
<220> FEATURE:
<223> OTHER INFORMATION: Description of Combined DNA/RNA Molecule:
      Synthetic siRNA antisense strand targeting human amphiregulin mRNA

<400> SEQUENCE: 2
cgaaccacaa auaccuggct t                                         21

<210> SEQ ID NO 3
<211> LENGTH: 21
<212> TYPE: DNA
<213> ORGANISM: Artificial Sequence

```
-continued

<220> FEATURE:
<223> OTHER INFORMATION: Description of Artificial Sequence: Synthetic
      siRNA antisense strand targeting human amphiregulin mRNA
<220> FEATURE:
<223> OTHER INFORMATION: Description of Combined DNA/RNA Molecule:
      Synthetic siRNA antisense strand targeting human amphiregulin mRNA

<400> SEQUENCE: 3
ccuggaagca guaacaugct t                                                    21
```

EGFR BLOCKING AGENTS FOR THE THERAPEUTIC TREATMENT OF MYOPIA

CROSS-REFERENCE TO RELATED APPLICATIONS

This patent application is a Divisional application of U.S. patent application Ser. No. 15/558,139, filed Sep. 13, 2017, which is a 35 U.S.C. § 371 application of International Application Serial No. PCT/EP2016/000460, filed Mar. 15, 2016, which applications are incorporated by reference. International Application Serial No. PCT/EP2016/000460 claims the benefit of priority of EP application serial No. EP 15000771.4, filed Mar. 16, 2015.

SEQUENCE LISTING

The instant application contains a Sequence Listing which has been filed electronically in ASCII format and is hereby incorporated by reference in its entirety. Said ASCII copy, created on Nov. 6, 2018, is named 08400_001US1_SL.txt and is 3,473 bytes in size.

The present invention relates to agents for use in the prophylactic or therapeutic treatment of myopia in a subject, wherein said agents are capable of decreasing epidermal growth factor receptor (EGFR) signaling and/or signaling of another receptor susceptible for amphiregulin in a subject in a direct or indirect manner. The present invention further relates to agents for use in the prophylactic or therapeutic treatment of hyperopia in a subject, wherein said agents are capable of increasing epidermal growth factor receptor (EGFR) signaling and/or signaling of another receptor susceptible for amphiregulin in a subject. Furthermore, the present invention relates to methods for the diagnosis of myopia or hyperopia in a subject, comprising the steps of (a) providing a biological sample from the subject; (b) determining the amphiregulin level in said sample; (c) comparing the level determined in step (b) to the amphiregulin levels found in emmetropic subjects or subjects going to be emmetropic; and (d) determining that the subject has myopia or is predisposed for the development of myopia in case the level determined in step (b) is higher than the amphiregulin levels found in emmetropic subjects or subjects going to be emmetropic; and determining that the subject has hyperopia or is predisposed for the development of hyperopia in case the level determined in step (b) is lower than the amphiregulin levels found in emmetropic subjects or subjects going to be emmetropic. Finally, the present invention relates to a method for identifying agents which associate with amphiregulin or fragments or variants thereof.

Myopia has rapidly emerged as a global health concern in the last three decades. It is one of the leading causes of visual impairment, and is associated with potentially blinding ocular complications including retinal detachment, myopic maculopathy, glaucoma and cataract. Evidence from family and twin studies supports the notion that myopia can be highly heritable in some families. On the other hand, the rapid upsurge of myopia in the last few decades in many parts of the world is likely to be a consequence of changes in lifestyle, such as the increasing intensity of education, particularly in urban East Asia. Parallel to the increase in the prevalence of myopia, the prevalence of hyperopia has declined. However, hyperopia has marked disadvantages such as the need for glasses for the distance and the near, and an increased prevalence of angle-closure glaucoma, age-related macular degeneration and diabetic retinopathy.

The process of emmetropization (i.e., sharp distant vision without glasses and without accommodative effect of the intraocular natural crystalline lens) of the growing eye from the stage of an infant towards the stage of an adult has not been cleared yet. The development of high axial myopia can be considered as an uncontrolled process of emmetropization, leading to an axial elongation of the globe. A globe too long in relationship to its refractive power focuses the image of an object, located in the distance, in front of the retina, so that the macula as the anatomical-optical center of the retina is not located in the focus and thus receives a blurred image with blurred borders. The same applies for a hyperopic globe which is too short in relationship to its refractive power and which focuses the image of an object, located in the distance, behind the retina.

At birth, the axial length of the eye is about 15 to 17 mm and elongates to approximately 23.6 to 24.0 mm in adults. Since most subjects in a mostly agrarian society are emmetropic, a finely tuned feed-back mechanism which sensors the sharpness of the image of the retina, communicates with the effector part by handing over the information of an axial length too short or too long, and governs the growth of the eye, in particular in its axial length, has to be present.

It is postulated that said finely tuned feed-back mechanism is located in the retina, since the retina is the only photosensitive part of the eye. Since the retinal photoreceptors as first element in the chain of photoreception and phototransduction are highly specialized (under experimental conditions, a single photoreceptor can detect the physically smallest unit of light energy, i.e., a photon), it is unlikely that the process of detecting haziness (defocus) of an image is located primarily within the photoreceptors. The next following groups of cells are the horizontal cells and amacrine cells in the inner nuclear layer. They have been shown to be associated with contrast formation and enhancement of the information obtained by the photoreceptors. The horizontal cells and amacrine cells form a dense horizontal network in the outer and inner plexiform layer of the retina. Since contrast is an essential part of detecting haziness of an image, it is likely that the horizontal/amacrine cells in association with retinal Willer cells, bipolar cells and other cells in the inner nuclear layer of the retina form the primary sensory part of the feed-back mechanism controlling eye growth. An image is sharp if its borders are sharp, i.e., out of two neighboring photoreceptors, one is fully activated by the incoming light of the object's border, and the next photoreceptor is completely dark due to the sharp border of the image on the retina. An image on the retina is blurred, if the decrease in the illumination of the photoreceptors at the border of the image decreases in a slope-like fashion across several neighboring photoreceptors. These differences (slope-like configuration versus edge-like shape) can be detected by the horizontal/amacrine cell system.

If the image of an object has been detected to be blurred (i.e., the length of the optical axis of the eye is not in agreement with the refractive power of the optic system of the eye), the next step is to differentiate whether the globe is too short (i.e., hyperopic) or too long (i.e., myopic). This can be achieved by the chromatic aberration of light within the eye: Short-wave length (blue) rays as compared to long-wavelength (red) rays are physiologically diffracted to a larger extent and thus have a shorter optical axis. If now a white (i.e., mixture of all spectral colors) image is fixed, its image will be projected onto the retina. If the blue-sensitive photoreceptors convey a sharper image than the red-sensitive photoreceptors do, the axial length (optical axis) is too short; if the red-sensitive photoreceptors convey a sharper image than the blue-sensitive photoreceptors do, the axial length (optical axis) is too long. The system can thus differentiate whether the axial growth of the eyes has to be increased or decreased.

Figure 1:
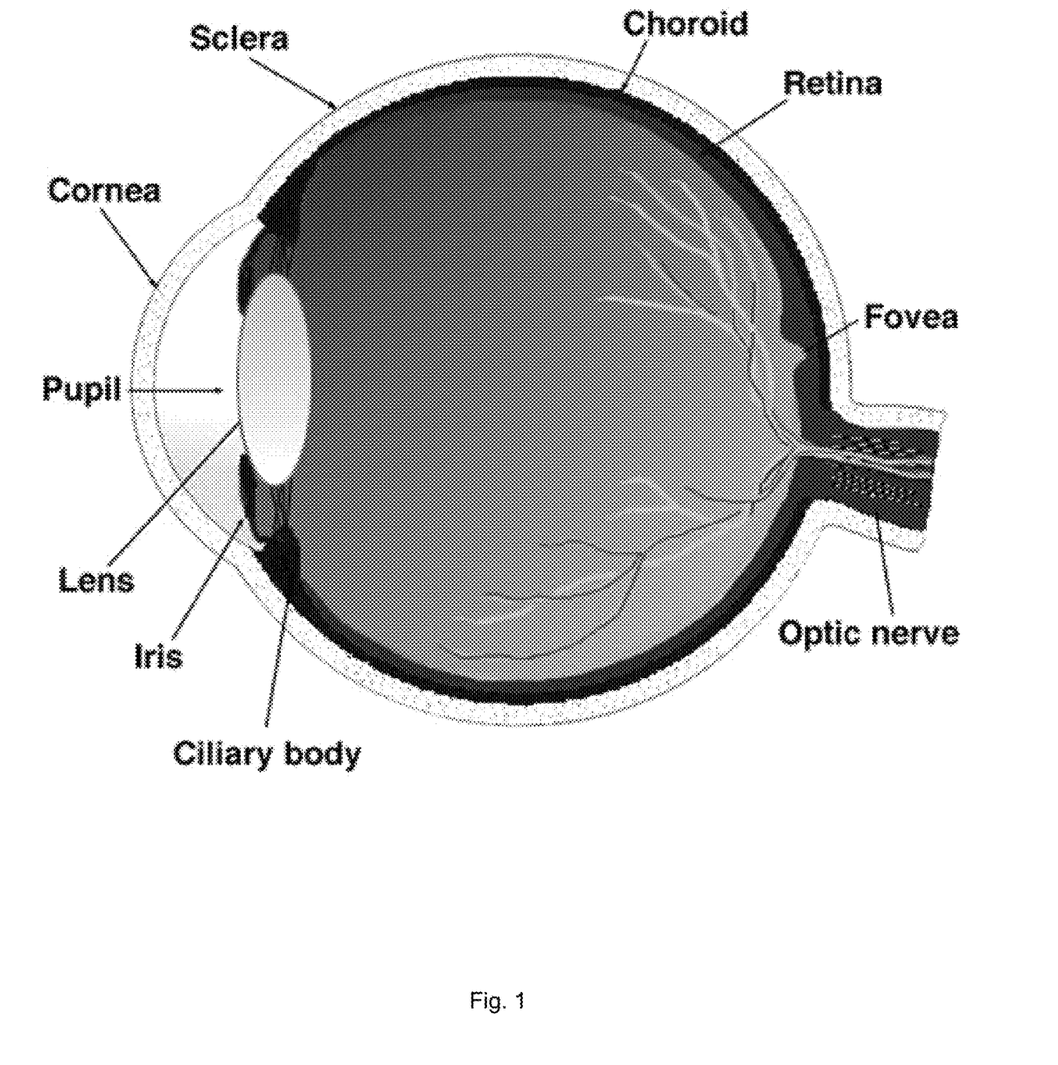
Figure 2:
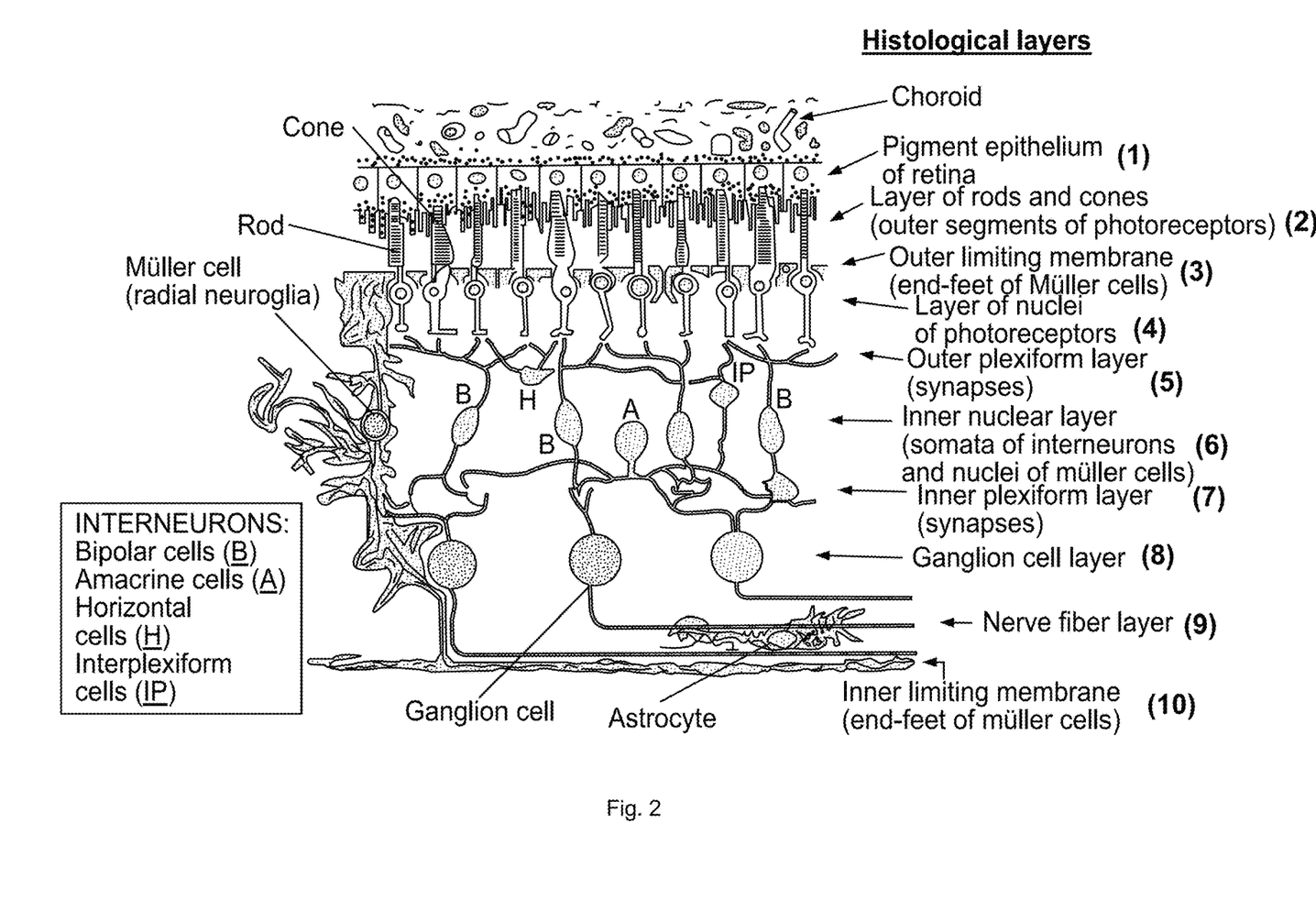

The effector of the process of emmetropization is postulated to be the retinal pigment epithelium (RPE) with its underlying Bruch's membrane (BM). This is in contrast to common belief that the sclera as the outer thick coat of the eye is the determinant of the axial elongation of the globe. In the course of a myopic axial elongation, the posterior sclera markedly thins from about 1 mm in emmetropic eyes to 0.1 mm in highly myopic eyes. In view of this marked thinning of the posterior sclera, it has commonly been accepted that the sclera is the primary effector of the excessive axial elongation in high myopia and may thus be responsible for the normal axial growth of the emmetropic eye. This assumption, however, is unlikely due to the following anatomical facts. In this context, FIGS. 1 and 2 provide an overview over the gross and microscopical anatomy of the eye.

If it were the sclera which primarily extends and makes the eye longer, the distance between the sclera and the inner layers, in particular Bruch's membrane (BM), should enlarge. The space between the sclera and BM is filled-up with the choroid. With increasing axial myopia, the choroid however gets markedly thinner (from about 250 pm to less than 30 pm) and the distance between BM and the sclera profoundly decreases. This may suggest that in high axial myopia the inner parts of the eye are not pulled outward (by an extending and elongating sclera), but are pushed outward by an internal process. Further, the sclera is very bradytrophic and contains only few nerves and blood vessels. It appears unlikely that a finely tuned mechanism such as the ocular emmetropization in which the axial length has to be controlled with an accuracy of less than 0.1 mm depends on such a little organized structure as the sclera. Also, the incoming light beams have to be focused onto the retinal photoreceptor outer segments very close to, or in, the RPE lying on the inner surface of BM. The sclera however, is separated from the RPE layer by the spongy choroid the thickness of which varies in dependence of factors such as daytime and presumably body position and cerebrospinal fluid pressure. This makes it furthermore unlikely that the sclera is the primary effector in the process of emmetropization.

In view of these findings, it is more likely that the RPE and BM form the effector part of the process of emmetropization. BM consists of the basal membrane of the RPE on its inner side, the basal membrane of the choriocapillaris on its outer side, and two collagenous layers separated from each other by an elastic layer in its center. Together with the RPE, BM forms the border between the choroid and retina, with the leaking choriocapillaris and the increased oncotic pressure on its choroidal side and with the retina-blood barrier and mostly edema free retinal tissue on its inner side. This watershed function of the BM is of high clinical importance since any defect in the BM-RPE complex leads to a leakage of fluid into the retinal tissue and secondary disruption of retinal function. BM is separated from the sclera by the loosely arranged spongy choroid and shows a physiologic opening as the inner part of the optic nerve head. Besides its barrier function, BM has biomechanical properties since it is a continuous inner shell which stretches from the ciliary body and indirectly from the scleral spur as its anterior anchoring to the peripapillary ring as its posterior fixation. The biomechanical properties of BM have not been explored yet. In a similar manner, the active changes occurring in BM during the growth of the eye have not been examined yet. Since BM is the basal membrane of the RPE, the RPE continuously produces BM material as is the case for any basal membrane. If the sclera cannot be the effector part of the emmetropization process, the only structure remaining to fulfill the function is the RPE/BM complex. The choroid itself is too spongy to be able to exert any pressure, and in a similar manner the retina is too spongy and too highly specialized for photoreception, phototransduction, image processing, and eventually transport of the information to the visual cerebral centers.

Thus, facts pointing to the RPE/BM complex as the primary effector for the process of emmetropization (and myopization) are: BM is not thinner in highly myopic eyes as compared to emmetropic eyes, the sclera however gets markedly thinned in highly myopic eyes. Further, in eyes with secondary high myopia due to congenital glaucoma, the myopic scleral thinning occurs also in the anterior segment of the eye in contrast to primary high myopia in which only the posterior sclera thins. Furthermore, in eyes with secondary high myopia due to congenital glaucoma, BM appears to be thinner than in eyes with primary myopia and thinner than in emmetropic eyes, suggesting that in secondary high myopia the increased elevated intraocular pressure (due to congenital glaucoma) within the first two years of life (during which the sclera—according to the existing model of thinking—or BM and the sclera—according to the mechanism described above—is passively still expandable) leads to a passive elongation of the ocular coats. Moreover, beyond an age of about 2 to 3 years, the scleral volume no longer increases and is then independent of the axial length. In contrast, scleral thickness, the more the closer to the posterior pole of the eye, decreases with longer axial length. This suggests that axial elongation beyond the physiological growth of the eye occurs by a rearrangement of the sclera and not by active scleral growth and increase in scleral volume. Finally, in a similar manner, beyond an age of about 2 to 3 years, the choroidal volume does not increase and is then independent of axial length. In contrast, choroidal thickness, the more the closer to the posterior pole of the eye, decreases with longer axial length. This suggests that axial elongation beyond the physiological growth of the eye occurs by a rearrangement of the choroid and not by active choroidal growth and increase in choroidal volume.

The RPE governs the axial elongation by the formation of new basal membrane material leading to the elongation and growth of BM. If, as pointed out above, the horizontal cells/amacrine cells in association with retinal Müller cells, bipolar cells and other cells in the inner nuclear layer of the retina are the sensory part of the process of emmetropization and myopization, and if the RPE/BM complex is the effector part, the question is how both parts communicate with each other. Since the transferal of such information by nerves is highly unlikely in the retina (nerves have not been found yet, short distance between the sensory part (horizontal cells/amacrine cells) and the effector part (RPE), potential continuous flow of fluid from the intraretinal space through the RPE/BM complex into the choroid), the signal transduction might take place by substances such as cytokines, chemokines, growth factors or similar proteins.

In view of the above, the technical problem underlying the present invention is to identify mediators of signal transduction between horizontal cells/amacrine cells and the RPE/BM complex, and, based on such findings, to provide agents that can be used in the prophylactic or therapeutic treatment of myopia and hyperopia.

The solution to the above technical problem is achieved by the embodiments characterized in the claims.

In particular, in a first aspect, the present invention relates to an agent that is capable of decreasing epidermal growth factor receptor (EGFR) signaling and/or signaling of another receptor susceptible for amphiregulin in a subject in a direct or indirect manner, for use in the prophylactic or therapeutic treatment of myopia in said subject.

Preferably, said agent is selected from the group consisting of:
(a) an isolated antibody, antibody fragment or antibody mimetic directed against native amphiregulin in said subject;
(b) an isolated antibody, antibody fragment or antibody mimetic directed against a native amphiregulin precursor in said subject;
(c) an isolated antibody, antibody fragment or antibody mimetic directed against EGFR in a blocking manner in said subject;
(d) an isolated antibody, antibody fragment or antibody mimetic directed against another receptor susceptible for amphiregulin in a blocking manner in a subject;
(e) an EGFR inhibiting agent; and
(f) a small interfering RNA (siRNA) agent capable of reducing the expression of amphiregulin in a subject.

Amphiregulin, also known as AREG, is a protein that in humans is encoded by the AREG gene. It is a member of the epidermal growth factor family, and is an autocrine growth factor as well as a mitogen for astrocytes, Schwann cells and fibroblasts. It is related to epidermal growth factor (EGF) and transforming growth factor alpha (TGF-alpha). Further, it usually interacts with the EGF receptor (EGFR) to promote the growth of normal epithelial cells, as well as with other receptors susceptible for amphiregulin. In the genome-wide joint meta-analysis underlying the present invention (cf. the data provided in the Examples of the present application), the AREG gene displayed the strongest correlation with refractive error. Further, amphiregulin is not a neurotransmitter (in contrast to e.g. gamma amino butyric acid), so that the secretion of amphiregulin does not interfere with the normal signal transduction in the visual afference. Furthermore, as a member of the family of epidermal growth factors, amphiregulin has an effect on epithelial cells such as the RPE. Based on these findings, amphiregulin has been identified in the present invention as a key mediator of axial elongation of the eye, due to its function as a signaling molecule between the sensory network in the middle retinal layers and the RPE/BM.

The term "decreasing epidermal growth factor receptor (EGFR) signaling and/or signaling of another receptor susceptible for amphiregulin in a subject in a direct or indirect manner" indicates the capability of the agents of the present invention to reduce the activity of the downstream signaling pathways of the respective receptors, either by a direct interaction with the receptors, as is e.g. the case for an antibody, antibody fragment or antibody mimetic directed against EGFR in a blocking manner, or by an indirect mechanisms, e.g. the inactivation of amphiregulin by a suitable antibody, antibody fragment or antibody mimetic directed against native amphiregulin, or the reduction of amphiregulin expression by a suitable siRNA.

In preferred embodiments, signaling is completely blocked, or is reduced by at least 10%, at least 20%, at least 30%, at least 40%, at least 50%, at least 60%, at least 70%, at least 75%, at least 80%, at least 85%, at least 90%, at least 92.5%, at least 95%, at least 97%, at least 98%, at least 98.5%, at least 99%, at least 99.25%, at least 99.5%, or at least 99.75% as compared to normal physiologic levels.

The term "isolated antibody or antibody fragment" as used herein relates to isolated, i.e., purified, native poly- or monoclonal antibodies or recombinantly produced poly- or monoclonal antibodies and fragments thereof. Antibody fragments are preferably selected from the group consisting of Fab fragments, F(ab')2 fragments and Fab' fragments. Methods for the isolation and/or purification of native antibodies are not particularly limited and are known in the art. Further, methods for the generation and expression of recombinant antibodies or antibody fragments are not particularly limited and are known in the art. Furthermore, methods for the generation of antibody fragments are not particularly limited and are known in the art.

The term "antibody mimetic" as used herein relates to proteinaceous compounds that, like antibodies, are capable of binding to a given target structure in a specific manner. Preferably, antibody mimetics are selected from the group consisting of single-chain variable fragments (scFv), single-domain antibodies, affibodies, affilins, affimers, affitins, anticalins, DARPins, monobodies, and peptide aptamers. Respective antibody mimetics and methods for producing the same are not particularly limited and are known in the art.

The term "antibody, antibody fragment or antibody mimetic directed against native amphiregulin/a native amphiregulin precursor/EGFR/another receptor susceptible for amphiregulin in a subject" as used herein indicates the ability of said antibodies, antibody fragments or antibody mimetics to bind to native amphiregulin, to a native amphiregulin precursor, to the EGFR, or to another receptor susceptible for amphiregulin in a subject in a specific manner, i.e., to recognize and bind a specific epitope of said amphiregulin, amphiregulin precursor, EGFR, or other receptor susceptible for amphiregulin. In this context, the term "antibody directed against amphiregulin/an amphiregulin precursor/EGFR/another receptor susceptible for amphiregulin" as used herein is intended to be equivalent to the term "anti-amphiregulin/anti-amphiregulin precursor/anti-EGFR/anti-receptor antibody".

Amphiregulin precursors are known in the art and include pro-amphiregulin, wherein the latter is a preferred amphiregulin precursor. Further, receptors susceptible for amphiregulin besides EGFR are known in the art.

The term "antibody, antibody fragment or antibody mimetic directed against EGFR/another receptor susceptible for amphiregulin in a blocking manner in a subject" as used herein indicates the ability of said antibodies, antibody fragments or antibody mimetics to inhibit the activation of EGFR or of another receptor susceptible for amphiregulin by amphiregulin in a direct or indirect manner, e.g. by sterically prohibiting the binding of amphiregulin to the EGFR or said other receptor or by inhibiting downstream effector functions of EGFR or said other receptor.

Antibodies, antibody fragments or antibody mimetics that are directed against native amphiregulin, e.g. native human amphiregulin, are not particularly limited and are known in the art. Further, antibodies that are directed against EGFR, e.g. human EGFR, in a blocking manner are not particularly limited and are known in the art. The same applies to antibodies, antibody fragments or antibody mimetics that are directed against amphiregulin precursors or against other receptors susceptible for amphiregulin in a blocking manner.

EGFR inhibiting agents for use in the present invention are not particularly limited and are known in the art. Respective agents are preferably selected from the group consisting of monoclonal antibody inhibitors of EGFR and small molecules to inhibit the EGFR tyrosine kinase.

Small interfering RNA (siRNA) agents and methods for producing and using the same are not particularly limited and are known in the art. According to the present invention, siRNA agents are capable of reducing the expression of amphiregulin in a subject. In preferred embodiments, the antisense strand of such siRNA agents, i.e., the strand targeting amphiregulin mRNA, consists of one of the sequences shown in SEQ ID NO: 2 and 3.

For use in the prophylactic or therapeutic treatment of myopia according to the present invention, the agent is preferably administered intravitreally, epicorneally, transcorneally, transsclerally, transconjunctivally, subconjunctivally, intraocularly, or systemically (e.g. orally, rectally, or intravenously). Respective methods for administration, as well as doses and dosage regimens are not particularly limited and are known in the art. Typical doses for an individual administration of e.g. antibodies, antibody fragments or antibody mimetics are in the range of 1 to 2 mg. As for e.g. intravitreal administration, the injected volume is typically in the range of 50 to 200 µl.

In a preferred embodiment, the subject to be treated is a human subject.

In particularly preferred embodiments according to the first aspect of the present invention, the agent is an antibody, antibody fragment or antibody mimetic directed against (i) native amphiregulin in a subject, or (ii) the epidermal growth factor receptor (EGFR) in a blocking manner in a subject.

In a second aspect, the present invention relates to an agent that is capable of increasing epidermal growth factor receptor (EGFR) signaling and/or signaling of another receptor susceptible for amphiregulin in a subject, for use in the prophylactic or therapeutic treatment of hyperopia in said subject.

Preferably, said agent is selected from the group consisting of:
 (a) isolated amphiregulin or a biologically active fragment or derivative thereof;
 (b) an isolated amphiregulin precursor or a biologically active fragment or derivative thereof;
 (c) an isolated antibody, antibody fragment or antibody mimetic directed against the epidermal growth factor receptor (EGFR) in an activating manner in said subject;
 (d) an isolated antibody, antibody fragment or antibody mimetic directed against another receptor susceptible for amphiregulin in an activating manner in a subject; and
 (e) an EGFR activating agent.

The term "increasing epidermal growth factor receptor (EGFR) signaling and/or signaling of another receptor susceptible for amphiregulin in a subject" indicates the capability of the agents of the present invention to increase the activity of the downstream signaling pathways of the respective receptors.

In preferred embodiments, signaling is increased by at least 10%, at least 20%, at least 30%, at least 40%, at least 50%, at least 60%, at least 70%, at least 80%, at least 90%, at least 100%, or more.

The term "isolated amphiregulin/amphiregulin precursor" as used herein relates to isolated, i.e., purified amphiregulin/amphiregulin precursor or recombinantly produced amphiregulin/amphiregulin precursor. Methods for the isolation and/or purification of native amphiregulin/amphiregulin precursor are not particularly limited and are known in the art. Further, methods for the generation and expression of recombinant amphiregulin/amphiregulin precursor are not particularly limited and are known in the art.

Amphiregulin precursors are known in the art and include pro-amphiregulin, wherein the latter is a preferred amphiregulin precursor. Further, receptors susceptible for amphiregulin besides EGFR are known in the art.

In preferred embodiments, said amphiregulin comprises or preferably consists of the amino acid sequence shown in SEQ ID NO: 1.

In this context, the term "biologically active fragment of amphiregulin/amphiregulin precursor" as used herein relates to fragments of amphiregulin/amphiregulin precursor that have one or more amino acid deletions with respect to native amphiregulin/amphiregulin precursor, while at the same time retaining the biological activity of binding to the EGF receptor or another receptor susceptible for amphiregulin and activating the same. Further, the term "derivative of amphiregulin/amphiregulin precursor" as used herein relates to polypeptides that are derived from native amphiregulin/amphiregulin precursor but have one or more amino acid substitutions, additions, or deletions with respect to native amphiregulin while at the same time retaining the biological activity of binding to the EGF receptor or another receptor susceptible for amphiregulin and activating the same. In this context, methods for determining the biological activity of amphiregulin or amphiregulin precursors are not particularly limited and are known in the art.

While the number of amino acid substitutions and/or additions and/or deletions is generally only limited by the above proviso concerning the biological activity of the resulting amphiregulin fragment or amphiregulin derivative polypeptide, it is preferable that the resulting fragment or polypeptide has at least 50%, at least 52.5%, at least 55%, at least 57.5%, at least 60%, at least 62.5%, at least 65%, at least 67.5%, at least 70%, at least 72.5%, at least 75%, at least 76.25%, at least 77.5%, at least 78.75%, at least 80%, at least 81.25%, at least 83.75%, at least 85%, at least 86.25%, at least 87.5%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.25%, at least 95.5%, at least 95.75%, at least 96%, at least 96.25%, at least 96.5%, at least 96.75%, at least 97%, at least 97.25%, at least 97.5%, at least 97.75%, at least 98%, at least 98.25%, at least 98.5%, at least 98.75%, at least 99%, at least 99.25%, or at least 99.5%, identity to native amphiregulin, e.g. native human amphiregulin according to SEQ ID NO: 1.

The terms "isolated antibody or antibody fragment" and "antibody mimetic" as used for this second aspect of the present invention are as defined above for the first aspect of the present invention. The same applies for the term "antibody, antibody fragment or antibody mimetic directed against EGFR/other receptor susceptible for amphiregulin".

The term "antibody, antibody fragment or antibody mimetic directed against EGFR/other receptor susceptible for amphiregulin in an activating manner in a subject" as used herein indicates the ability of said antibodies, antibody fragments or antibody mimetics to activate EGFR or another receptor susceptible for amphiregulin independently of amphiregulin, i.e., to trigger downstream effector functions of EGFR or said other receptor susceptible for amphiregulin.

Antibodies, antibody fragments or antibody mimetics that are directed against EGFR, e.g. human EGFR, in an activating manner are not particularly limited and are known in the art. The same applies to antibodies, antibody fragments or antibody mimetics that are directed against other receptors susceptible for amphiregulin in an activating manner.

EGFR activating agents for use in the present invention are not particularly limited and are known in the art. Respective agents are preferably selected from the group consisting of members of the epidermal growth factor (EGF) family (including transforming growth factor-α (TGF-α), amphiregulin (AR), epiregulin (EPR), epigen, betacellulin (BTC), neuregulin-1 (NRG1), neuregulin-2 (NRG2) neuregulin-3 (NRG3), and neuregulin-4 (NRG4)).

For use in the prophylactic or therapeutic treatment of hyperopia according to the present invention, the agent is preferably administered intravitreally, epicorneally, transcorneally, transsclerally, transconjunctivally, subconjunctivally, intraocularly, or systemically (e.g. orally, rectally, or intravenously). Respective methods for administration, as well as doses and dosage regimens are not particularly limited and are known in the art. Typical doses for an individual administration of e.g. antibodies, antibody fragments or antibody mimetics, or of amphiregulin are in the range of 1 to 2 mg. As for e.g. intravitreal administration, the injected volume is typically in the range of 50 to 200 µl.

In a preferred embodiment, the subject to be treated is a human subject.

In particularly preferred embodiments according to the second aspect of the present invention, the agent is isolated amphiregulin or a biologically active fragment or derivative thereof, or an isolated antibody, antibody fragment or antibody mimetic directed against the epidermal growth factor receptor (EGFR) in an activating manner in a subject.

In a further aspect, the present invention relates to a method for the prophylactic or therapeutic treatment of myopia in a subject, comprising the step of administering a therapeutically effective amount of an agent as defined for the first aspect of the present invention to said subject. In yet a further aspect, the present invention relates to a method for the prophylactic or therapeutic treatment of hyperopia in a subject, comprising the step of administering a therapeutically effective amount of an agent as defined for the second aspect of the present invention to said subject.

In both of these aspects, the (i) agents, (ii) antibody, antibody fragment or antibody mimetic directed against native amphiregulin, (iii) antibody, antibody fragment or antibody mimetic directed against a native amphiregulin precursor, (iv) antibody, antibody fragment or antibody mimetic directed against EGFR in a blocking manner, (v) antibody, antibody fragment or antibody mimetic directed against another receptor susceptible to amphiregulin in a blocking manner, (vi) amphiregulin or a biologically active fragment or derivative thereof, (vii) amphiregulin precursor or a biologically active fragment or derivative thereof, (viii) antibody, antibody fragment or antibody mimetic directed against the epidermal growth factor receptor (EGFR) in an activating manner, (ix) antibody, antibody fragment or antibody mimetic directed against another receptor susceptible for amphiregulin in an activating manner, (x) EGFR inhibiting agent, (xi) EGFR activating agent, (xii) siRNA agent, (xiii) administration, and (xiv) subject are as defined for the first two aspects of the present invention. Further, respective therapeutically effective amounts are known in the art.

In a further aspect, the present invention relates to a method for the diagnosis of myopia or hyperopia, or of a predisposition for the development of myopia or hyperopia, in a subject, comprising the steps of:
(a) providing a biological sample from the subject;
(b) determining the amphiregulin level in said sample;
(c) comparing the level determined in step (b) to the amphiregulin levels found in emmetropic subjects or subjects going to be emmetropic; and
(d) determining that the subject has myopia or is predisposed for the development of myopia in case the level determined in step (b) is higher than the amphiregulin levels found in emmetropic subjects or subjects going to be emmetropic; and determining that the subject has hyperopia or is predisposed for the development of hyperopia in case the level determined in step (b) is lower than the amphiregulin levels found in emmetropic subjects or subjects going to be emmetropic.

Types of biological samples for practicing this method are known to a person skilled in the art and include blood, blood serum, blood plasma, and cerebrospinal fluid. Further, methods for determining the amphiregulin level in a biological sample are not particularly limited and are known in the art.

In a final aspect, the present invention relates to a method for identifying agents which associate with amphiregulin or fragments or variants thereof, comprising the steps of:
(a) contacting said amphiregulin or fragments or variants thereof, or a recombinant host cell expressing amphiregulin or fragments or variants thereof, with a test compound and
(b) analyzing the ability of said test compound to bind to amphiregulin or fragments or variants thereof.

In preferred embodiments of this method, the ability of said test compound to bind to amphiregulin or a fragment or variant thereof or the ability of said test compound to inhibit binding of said amphiregulin or a fragment or variant thereof to EGFR or any other receptor susceptible for amphiregulin or a variant thereof is analyzed.

In further preferred embodiments, said method further comprises the step of formulating said compound or a pharmaceutically acceptable salt thereof with one or more pharmaceutically acceptable excipient(s) and/or carrier(s).

In this context, methods for generating recombinant host cell expressing amphiregulin or fragments or variants thereof, respective amphiregulin fragments or amphiregulin variants, methods for analyzing the ability of said test compound to bind to amphiregulin or fragments or variants thereof, and methods for analyzing the ability of said test compound to inhibit binding of said amphiregulin or a fragment or variant thereof to EGFR or any other receptor susceptible for amphiregulin or a variant thereof, are not particularly limited and are known in the art.

In the genome-wide joint meta-analysis underlying the present invention (cf. the data provided in the Examples of the present application), further genes and genetic markers that correlated with refractive error in addition to amphiregulin have been identified. These are (i) FAM150B (family with sequence similarity 150 member 2) which interacts with leukocyte tyrosine kinase (LTK), (ii) LINC00340, (iii) FBN1 (fibrillin 1), (iv) MAP2K1 (mitogen-activated protein kinase 1) which interacts with muscarinic receptors, (v) ARID2 (AT-rich interactive domain 2) which is a subunit of the chromatin remodeling complex PBAF, (vi) SLC14A2 (solute carrier family 14 member 2) which is an urea transporter, (vii) GABRR1 which is a receptor for gamma-aminobutyric acid (GABA), and (viii) PDE10A which is an enzyme that can hydrolyze cAMP/cGMP. These can be used in the present invention in an analogous manner to amphiregulin as described herein.

The present invention is based on the finding of a mechanism in the development of myopia as state-out-of-control of the physiological process of emmetropization of the eye. Emmetropization of the eye refers to the process of controlled increase in the ocular dimensions (axial length, horizontal and vertical globe diameters, curvature of the anterior and posterior lens surface, position of the lens, curvature of the anterior and posterior surface of the cornea, refractive indices in the various optic media, distances between the various elements of the optic media of the eye). The mechanism includes a sensory part which detects that the image of objects on the retina is not sharply focused and blurry. The detection of a defocused image will be in the layer of horizontal cells and amacrine cells in the middle layers of the retina. The network provided by the intertwining of the photoreceptor axons, the axons and dendrites of the horizontal and amacrine cells and bipolar cells, in close association with the retinal Willer cells, will detect whether the edges of the images are sharp or blurry. This process may partially be associated with contrast sensitivity and contrast enhancement or contrast suppression physiologically taking place in these retinal layers.

If the sharpness or haziness of the image edges has been detected, the cells in the intertwining network will also sensor whether the edges for blue images or for red images are sharper, since light of blue color, green color and red color is sensed by three different types of cone photoreceptors. Using the physical principle of chromatic aberration, a sharp image in the blue range instead of the red range indicates that the axial length of the eye is too short, whereas a sharp image in the red range instead of the blue range indicates that the axial length of the eye is too long. Correspondingly, in the case of a sharp blue image and defocused red image, the network of cells will give a signal to the effector element in the process emmetropization of the eye to increase the ocular axial length. In the case of a sharp red image and defocused blue image, the network of cells will give a signal to the effector element in the process emmetropization of the eye to stop the increase in ocular length or to decrease the speed in increasing the axial length during the physiological growing of the eye.

Structures in the growing eye, which are involved in governing axial elongation during the physiological growth of the eye are the retinal pigment epithelium cells (RPE), which are close enough to the retinal network in the middle retinal layers to receive signals, are pluripotent due to their relatively low degree of specialization during embryogenesis, and above all form the inner part of Bruch's membrane (BM) as their basal membrane. BM can be regarded as a biomechanically important inner shell in the eye, connected to the pars *plicata* of the ciliary body with the ciliary muscle and indirectly to the scleral spur in the anterior segment, and to the peripapillary ring of the optic nerve head in the posterior segment. If the network in the middle retinal layers gives a signal to the RPE cells to produce more basal membrane, this results in the deposition of more basal membrane material in the inner layer of BM which subsequently will elongate. Elongation of BM means that BM pushes the sclera more outward by transmitting the growth-related pressure through the spongy choroid onto the sclera. Further, it secondarily leads to a thinning of the choroid. Correspondingly, axial elongation after an age of 2 to 3 years (i.e., after the end of the physiological growth of the globe) is associated with a thinning of the sclera and choroid, however it is not associated with an increase in the volume of sclera and choroid, contradicting an active role of both tissues in the process of emmetropization. As a corollary, BM, in contrast to the choroid and sclera, does not decrease in thickness in axial elongation pointing to the active role of BM in shaping and fine-tuning the final shape and length of the eye.

The signaling pathway between the sensory network in the middle retinal layers and the RPE/BM as the effector part uses molecules such as cytokines, chemokines, growth factors or similar proteins, which either give an impulse to the RPE to lay down more basal membrane material or to decrease the production of this material. In this context, amphiregulin has been identified in the present invention as one of these molecules and as a key mediator of axial elongation of the eye.

The figures show:

FIG. 1:

Gross anatomy of the eye.

Vertical sagittal section of the adult human eye.

FIG. 2:

Microscopical anatomy of the eye.

Organization of the retina in a schematic vertical section. Interneurons are designates as (B) bipolar cells, (A) amacrine cells, (H) horizontal cells, and (IP) interplexiform cells. In reality, the retina is packed with cells, and there is hardly any extracellular space. The ten layers of the retina are listed on the right-hand side of the figure: (1) Pigment epithelium of retina, (2) layer of rods and cones (outer segments of photoreceptors), (3) outer limiting membrane (end-feet of Müller cells), (4) layer of nuclei of photoreceptors, (5) outer plexiform layer (synapses), (6) inner nuclear layer (somata of interneurons and nuclei of Müller cells), (7) inner plexiform layer (synapses), (8) ganglion cell layer, (9) nerve fiber layer, (10) inner limiting membrane (end-feet of Müller cells). The potential space between the pigment epithelium and the layer of rods and cones is the "optic ventricle", the remnant of the cavity of the optic vesicle.

FIG. 3A:

Manhattan plot of $-\log_{10}(P)$ for the Joint meta-analysis on SNP and SNP×education effects on spherical equivalent in European Ancestry populations.

The upper horizontal dashed line indicates the genome-wide significance level of $p<5\times10^{-8}$. The lower horizontal dashed line indicates the suggestive significance level of $p<1\times10^{-5}$. Only novel loci reaching genome-wide significance are labeled.

FIG. 3B:

Manhattan plot of $-\log_{10}(P)$ for the Joint meta-analysis on SNP and SNP×education effects on spherical equivalent in Asian populations.

The upper horizontal dashed line indicates the genome-wide significance level of $p<5\times10^{-8}$. The lower horizontal dashed line indicates the suggestive significance level of $p<1\times10^{-5}$. Only novel loci reaching genome-wide significance are labeled.

The present invention discloses the following sequences:

```
Human amphiregulin amino acid sequence
                                                                  SEQ ID NO: 1
MRAPLLPPAP VVLSLLILGS GHYAAGLDLN DTYSGKREPF SGDHSADGFE VTSRSEMSSG    60

SEISPVSEMP SSSEPSSGAD YDYSEEYDNE PQIPGYIVDD SVRVEQVVKP PQNKTESENT   120
```

-continued

```
SDKPKRKKKG GKNGKNRRNR KKKNPCNAEF QNFCIHGECK YIEHLEAVTC KCQQEYFGER    180

CGEKSMKTHS MIDSSLSKIA LAAIAAFMSA VILTAVAVIT VQLRRQYVRK YEGEAEERKK    240

LRQENGNVHA IA                                                       252
``` siRNA antisense strand targeting human amphiregulin mRNA
SEQ ID NO: 2

CGAAC CACAA AUACC UGGCT T siRNA antisense strand targeting human amphiregulin mRNA
SEQ ID NO: 3

CCUGG AAGCA GUAAC AUGCT T

The present invention will be further illustrated by the following examples without being limited thereto.

EXAMPLES

Experimental Procedures

Study Populations

From the Consortium of Refractive Error and Myopia (CREAM), a total of 34 studies comprising 40,036 individuals of European ancestry from 25 studies and 10,315 individuals of Asian ancestry from 9 studies were recruited. Individuals aged less than 20 years old were excluded, as well as those who had undergone cataract surgery, laser or other intra-ocular procedures that could alter refraction. Many of these studies were also included in the previous CREAM genome-wide association study (GWAS) on spherical equivalent. All studies adhered to the tenets of the Declaration of Helsinki and were approved by their local research ethics committees. All participants provided a written, informed consent before the start of the study.

Phenotyping and Education Levels

Participants in the included studies underwent complete ophthalmological examination. Non-dilated refraction was measured by auto-refraction and/or subjective refraction. Spherical equivalent was calculated as the sphere power plus half of the cylinder power for each eye. The mean spherical equivalent of the right and left eyes was used as a quantitative outcome. When data from only one eye was available, the spherical equivalent of that eye was used. For education, subjects reported the highest level of education achieved, or the years of schooling through a self-reported questionnaire or in an interview.

Education for all participants was dichotomized into a higher education group consisting of those who had completed at least higher secondary education, polytechnic, or 12 years spent in formal education, and a lower education group including individuals who had only completed lower secondary education or less, or with <12 years of formal education. In four cohorts of relatively young European participants (total sample size of 2,349), almost all had completed 12 or more years of schooling. It was thus chosen to categorize individuals with tertiary or university education as the higher education group. Sensitivity analysis excluding these four cohorts did not appreciably change meta-analysis results.

Genotyping and Imputation

Each study applied stringent quality control filters for GWAS. In general, individuals reflecting duplicates, low call rate (<95%), gender mismatch, or population outliers we excluded. SNPs were excluded in cases of low genotyping call rate (>5% missingness), monomorphic SNPs, with MAF<1%, or in Hardy-Weinberg disequilibrium (p-value<$10^{-6}$). After quality control (QC) filtering, the array genotypes of each study were imputed using the 1000 Genomes Project data as reference panels (build 37, phase 1 release, March 2012) with the software Minimac or IMPUTE. SNPs which passed imputation quality thresholds (MACH: $r^2$>0.5 or IMPUTE info score>0.5) and with minor allele frequency 5% were carried forward for the meta-analysis.

Statistical Models

For each study, a linear regression model at each genotyped or imputed SNP was constructed, with the mean spherical equivalent as the outcome. An additive genetic model was assumed where the number of risk alleles is an ordinal variable (0, 1 and 2) for directly genotyped SNPs, or a continuous variable of allele dosage probability ranging from 0 to 2 for imputed SNPs. The primary analytic model included SNP, education, a SNP×education interaction term, as well as age and sex as covariates. Additional adjustments for the top principal components of genomic marker variations were performed in individual studies when applicable (i.e., when there was evidence of population stratification).

The following additive genetic model was used to test for a joint effect of SNP ($\beta_{SNP}$) and SNP×education interaction ($\beta_{SNP \times education}$) on mean spherical equivalent:

$$Y = \beta_0 + \beta_{SNP} \times SNP + \beta_{education} \times \text{Education} + \beta_{SNP \times education} \times SNP \times \text{Education} + \beta_c \times Cov + \varepsilon \quad \text{(Model 1)}$$

where Y is the mean spherical equivalent, education is a dichotomous variable (0=lower education group and 1=higher education group); Coy is a set of covariates such as age, sex and first top five principal components when applicable. For family-based studies, the kinship matrix was estimated empirically from the SNP data and included as a random effect in the generalized mixed model. To test an effect of SNP×education interaction, $\beta_{SNP \times education}$ was assessed from Model 1.

The linear regression analyses in each study were conducted with Quicktest (toby.freeshell.org/software/quicktest.shtml) or ProbABEL (www.genabel.org/packages/ProbABEL) for the unrelated samples, and MixABEL (www.genabel.org/packages/MixABEL) for family-based data. The command 'robust' was used in the above software to calculate the robust ('sandwich', Huber-White) standard errors of $\beta_{SNP}$ and $\beta_{SNP \times education}$, and error covariance of $\beta_S$, to correct the potential inflation of false positive rate for the interaction p-value.

In addition, each study also tested the main effect of education on spherical equivalent by adjusting for age and gender using the linear regression model:

$$Y = \beta_0 + \beta_{education} \times \text{education} + \beta_c \times Cov + \varepsilon \quad \text{(Model 2)}$$

where the definition of the variables is the same as in Model 1.

GWAS Meta-Analyses

The joint meta-analysis (JMA) approach was adopted to simultaneously test both main SNP effects and SNP×education interactions for spherical equivalent with a fixed-effect model, using SNP and SNP×education regression coefficients and a betas' covariance matrix from each study. A Wald statistic, following a chi-square distribution with two degrees of freedom, was used to test the joint significance of the SNP and SNP×education regression coefficients. The JMA was performed with METAL (www.sph.umich.edu/csg/abecasis/metal/), using a script patch. A Cochran's Q test was used to assess heterogeneity of the beta coefficients across studies for the SNP and interaction effects. To test for interaction between the SNP and education, a secondary meta-analysis of the SNP×education interaction effects for spherical equivalent (one degree of freedom) with a fixed-effects model using inverse-variance weighting in METAL was conducted; this is a traditional meta-analysis to investigate SNP×education interactions per se. Effects and standard error of the SNP ($\beta_{SNP}$) on spherical equivalent in the lower education group and higher education ($\beta_{SNP}$+ $\beta_{SNP \times education}$) were derived from the JMA output.

A meta-regression was performed to explore sources of heterogeneity in the meta-analysis for three loci showing G×E interactions (R package 'metafor'; www.rproject.org/). Meta-regression included the following study-specific variables as covariates: study sample size, proportion of individuals in the higher education group, average spherical equivalent, education main effects, ethnicity, study design, study year, and average age.

The study-specific genomic control inflation factors $\lambda_{gc}$ for the joint test for SNP and interaction term ranged from 1.009 to 1.125 with an average of 1.019, calculated by the ratio of the observed median chi-square divided by the expected median of the 2df chi-square distribution (1.382). Genomic control (GC) correction was applied to chi-square statistics in each individual study. For three studies of small sample sizes (N<500) and $\lambda_{gc}$ greater than 1, SNPs showing significant joint P value<1×10$^{-5}$ were further excluded prior to starting the meta-analysis, but neither the main effects nor the interaction effects supporting such an association. Quantile-quantile (QQ) plots of the p-values showed only modest inflation of the test statistics in the JMA (Europeans: $\lambda_{meta}$=1.081; Asians: $\lambda_{meta}$=1.053; Combined: $\lambda_{meta}$=1.092, similar to previous genome-wide JMA studies with comparable sample sizes. A small number of markers in the meta-analysis with $P_{HET}$<0.0001 was excluded. The $\lambda_{gc}$ for the SNP×education interaction term in the individual studies ranged from 1.01 to 1.08, indicating little evidence of test statistic inflation for each study.

Annotation of Genetic Variants

The coordinates and variant identifiers are reported on the NCBI B37 (hg19) genome build, and annotated using UCSC Genome Browser. Variants within each of the linkage disequilibrium (LD) blocks ($r^2$>0.8) in European and Asian populations of the 1000 Genomes Project (100 Kb flanking the top SNP; hg19) were identified to apply functional annotations with experimental evidence of transcription regulation using HaploReg (www.broadinstitute.org/mammals/haploreg/haploreg.php) and Encyclopedia of DNA Elements (ENCODE) data.

Gene Expression in Human Tissues GWAS Meta-Analyses and SNP Function Annotation

To assess gene expression in human tissues, the Ocular Tissue Database (genome.uiowa.edu/otdb) and the EyeSAGE database were examined. The estimated gene and exome level abundances are available online. Normalization of gene expression used the Probe Logarithmic Intensity Error (PLIER) method with GC-background correction.

Example 1

Education and its Main Effects on Spherical Equivalent

Baseline characteristics of 50,351 participants from 34 studies in our meta-analysis show that a total of 40,036 of subjects were of European ancestry and 10,315 were of Asian ancestry; the age of the participants ranged from 20 to 99 years. Among Europeans, the proportions of participants who completed higher secondary education ranged from 16.0% to 94.4% with an average of 50.7%. In Asians, the proportions of individuals who completed higher secondary education ranged from 6.7% to 75.9% with an average of 30.0%. Across all studies, individuals in the higher education group had a spherical equivalent refractive error that was on average 0.59 diopters (D) more myopic, or less hyperopic, compared to those in the lower education group ($\beta$=−0.59; 95% CI: −0.64, −0.55). High education level was associated with a two-fold more myopic spherical equivalent in individuals of Asian as compared to European ancestry (Asians: $\beta$=−1.09, 95% CI: −1.20, −0.98; Europeans: $\beta$=−0.49, 95% CI: −0.54, −0.44.

Example 2

Joint Meta-Analysis in Europeans

Figure 3A:
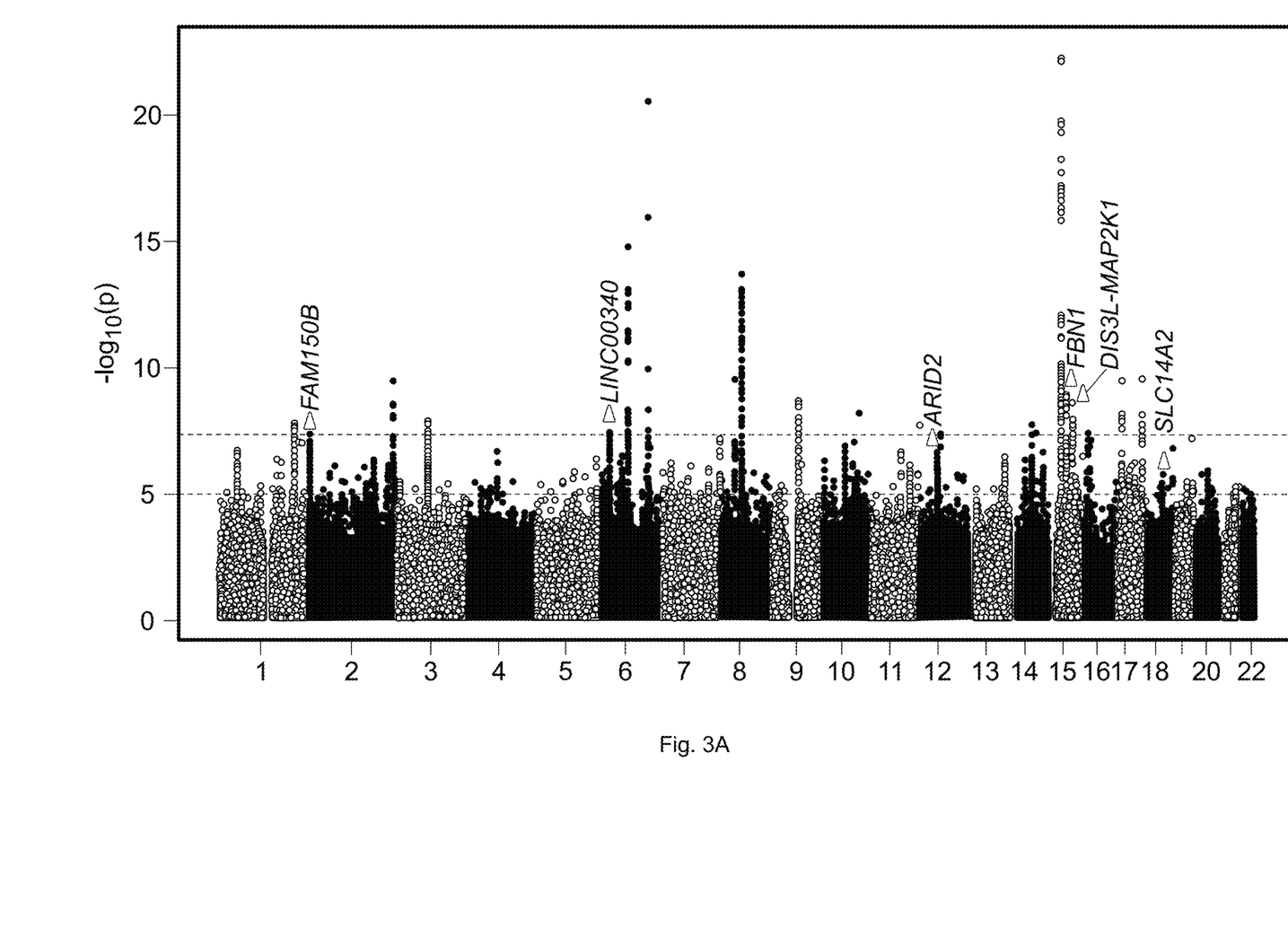

The genome-wide joint analysis for SNP main effect and SNP×education interaction by JMA in 40,036 European Ancestry individuals showed association with spherical equivalent at 9 previously implicated loci. Further, 4 previously unreported loci associated with spherical equivalent were also identified achieving genome-wide significance (P for JMA<5.0×10$^{-8}$; Table 1 and FIG. 3 A): FAM150B, LINC00340, FBN1, and DIS3L-MAP2K1. Two of them (FAM150B and DIS3L-MAP2K1) were replicated in Asians (P for JMA<0.05; refer to the following section). Little evidence of heterogeneity in JMA was noted across studies (Q test: $P_{het}$≥0.086). The significant association for JMA at these loci in Europeans was primarily due to SNP effects in both lower and higher education strata (4.40×10$^{-8}$≤P≤1.35×10$^{-6}$, 7.61×10$^{-11}$≤P≤1.75×10$^{-8}$, respectively). SNP×education interaction was not significant (P for interaction 0.208). The estimated effect sizes of SNP effects on spherical equivalent were highly similar across education strata.

TABLE 1

Six genetic loci associated with spherical equivalent from the joint meta-analysis in the European populations and combined analysis.

| SNP (Chr: BP) | Gene | Allele | FREQ | Subgroup | Europeans (n = 40,306) | |
|---|---|---|---|---|---|---|
| | | | | | β | P |
| rs60843830 (2: 286756) | FAM150B | C/G | 0.66/0.74 | JMA | | 3.71 × 10$^{-8}$ |
| | | | | Lower educaton | −0.11 | 4.73 × 10$^{-8}$ |
| | | | | Higher education | −0.09 | 1.75 × 10$^{-6}$ |
| rs10946507 (6: 22100367) | LINC00340 | A/G | 0.47/0.36 | JMA | | 3.07 × 10$^{-8}$ |
| | | | | Lower educaton | −0.08 | 7.08 × 10$^{-7}$ |
| | | | | Higher education | −0.09 | 1.19 × 10$^{-8}$ |

TABLE 1-continued

Six genetic loci associated with spherical equivalent from the joint
meta-analysis in the European populations and combined analysis.

| | | | | | | |
|---|---|---|---|---|---|---|
| rs8023401 (15: 48703823) | FBN1 | G/A | 0.83/0.85 | JMA | | $1.66 \times 10^{-9}$ |
| | | | | Lower educaton | −0.15 | $4.40 \times 10^{-8}$ |
| | | | | Higher education | −0.16 | $7.61 \times 10^{-11}$ |
| rs16949788 (15: 66590037) | DIS3L-MAP2K1 | T/C | 0.91/0.94 | JMA | | $1.34 \times 10^{-8}$ |
| | | | | Lower educaton | −0.15 | $1.35 \times 10^{-6}$ |
| | | | | Higher education | −0.17 | $1.89 \times 10^{-9}$ |
| rs10880855 (12: 46144855) | ARID2 | T/C | 0.51/0.43 | JMA | | $7.83 \times 10^{-7}$ |
| | | | | Lower educaton | −0.09 | $1.26 \times 10^{-7}$ |
| | | | | Higher education | −0.07 | $1.60 \times 10^{-8}$ |
| rs10853531 (18: 42824449) | SLC14A2 | G/A | 0.70/0.77 | JMA | | $7.82 \times 10^{-6}$ |
| | | | | Lower educaton | −0.11 | $1.27 \times 10^{-6}$ |
| | | | | Higher education | −0.08 | $2.12 \times 10^{-6}$ |

| | Europeans (n = 40,306) | | Asians (n = 10,315) | | All (n = 50,351) | |
|---|---|---|---|---|---|---|
| SNP (Chr: BP) | $P_{het}$ | β | P | $P_{het}$ | β | P | $P_{het}$ |
| rs60843830 (2: 286756) | 0.086 | | 0.0131 | 0.980 | | $1.27 \times 10^{-9}$ | 0.395 |
| | | −0.09 | 0.010 | | −0.10 | $1.65 \times 10^{-9}$ | |
| | | −0.06 | 0.509 | | −0.09 | $9.83 \times 10^{-7}$ | |
| rs10946507 (6: 22100367) | 0.213 | | 0.433 | 0.396 | | $2.24 \times 10^{-8}$ | 0.249 |
| | | −0.04 | 0.313 | | −0.08 | $6.13 \times 10^{-7}$ | |
| | | −0.08 | 0.450 | | −0.09 | $1.20 \times 10^{-8}$ | |
| rs8023401 (15: 48703823) | 0.130 | | 0.572 | 0.979 | | $2.85 \times 10^{-9}$ | 0.495 |
| | | −0.06 | 0.304 | | −0.13 | $8.17 \times 10^{-8}$ | |
| | | −0.03 | 0.828 | | −0.14 | $2.02 \times 10^{-9}$ | |
| rs16949788 (15: 66590037) | 0.721 | | 0.0042 | 0.219 | | $2.19 \times 10^{-8}$ | 0.245 |
| | | 0.21 | 0.103 | | −0.13 | $4.88 \times 10^{-6}$ | |
| | | −0.59 | 0.014 | | −0.16 | $3.90 \times 10^{-9}$ | |
| rs10880855 (12: 46144855) | 0.790 | | 0.019 | 0.779 | | $4.38 \times 10^{-8}$ | 0.867 |
| | | −0.06 | 0.067 | | −0.09 | $8.42 \times 10^{-9}$ | |
| | | −0.16 | 0.033 | | −0.07 | $3.55 \times 10^{-6}$ | |
| rs10853531 (18: 42824449) | 0.052 | | 0.0023 | 0.812 | | $2.54 \times 10^{-8}$ | 0.111 |
| | | −0.15 | $9.01 \times 10^{-4}$ | | −0.11 | $3.38 \times 10^{-9}$ | |
| | | −0.11 | 0.288 | | −0.09 | $7.14 \times 10^{-6}$ | |

JMA, joint meta-analysis on SNP association and SNP × education on spherical equivalent; the effects estimates presented are derived from the JMA for the lower and higher education group. $P_{het}$, p-value for the test of heterogeneity at each SNP; Allele is listed as risk allele/other allele; FREQ, allele frequency of the risk allele in Asian/European cohorts.

Example 3

Joint Meta-Analysis in Asians

Figure 3B:
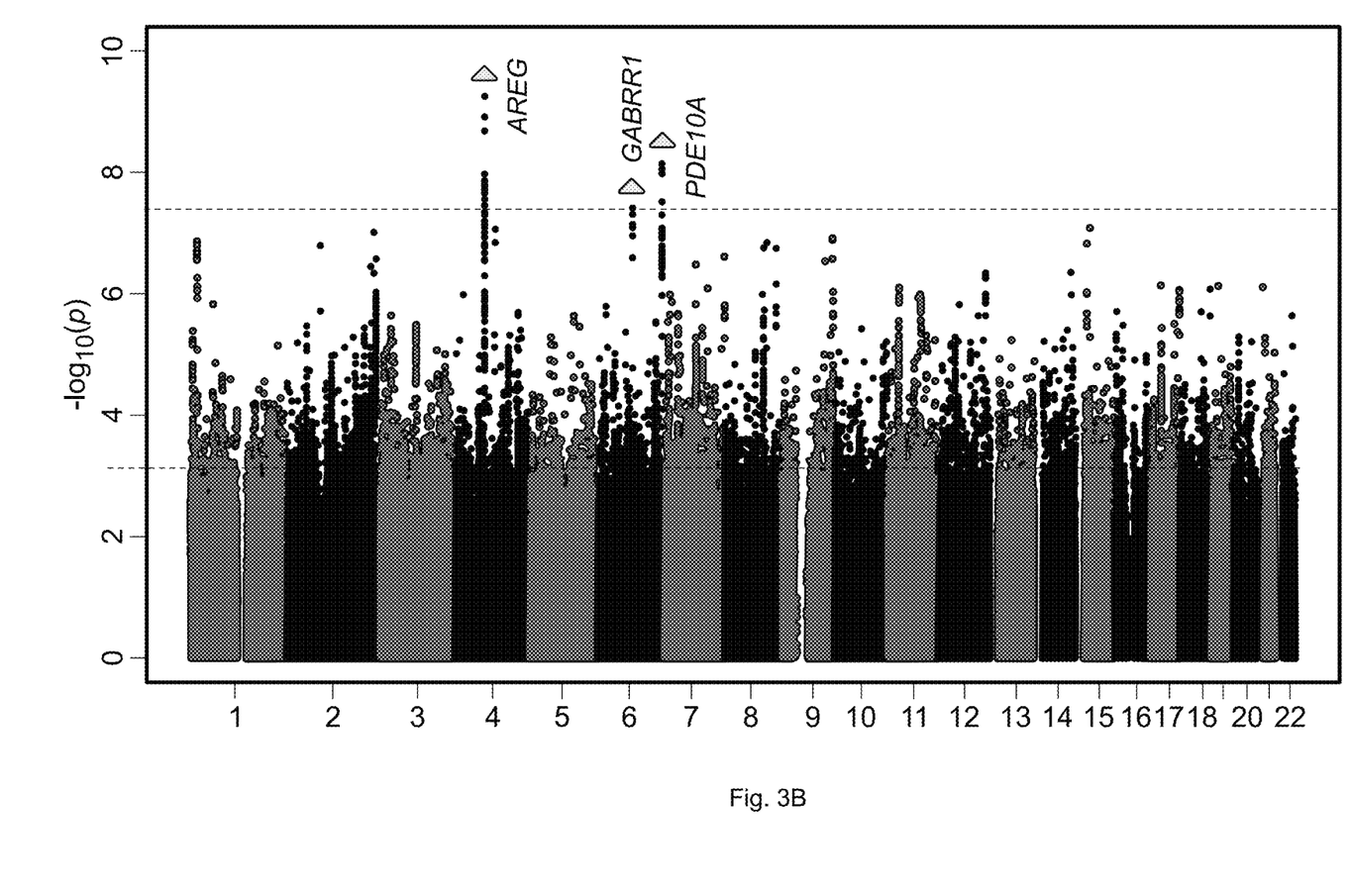

The JMA for spherical equivalent in 10,315 individuals from the Asians cohorts identified genome-wide significant association for three genes: AREG, GABRR1 and PDE10A (P for JMA<$5.0 \times 10^{-8}$; Table 2 and FIG. 3 B). SNP×education interaction effects associated with spherical equivalent were observed at all three loci (P for interaction $8.48 \times 10^{-5}$). The genotype and phenotype associations were highly significant in the higher education stratum ($1.97 \times 10^{-10}$ $8.16 \times 10^{-8}$) but were considerably weaker in the lower education stratum ($0.008 \leq P \leq 0.243$). There was no evidence of inter-study heterogeneity at index SNPs within AREG, GABRR1 or PDE10A (Q test: $P_{het} \geq 0.122$).

GABRR1 and PDE10A index SNPs were not associated with spherical equivalent in European samples, for either the JMA joint test, SNP main effect, or SNP×education interaction (Table 2). AREG SNP rs12511037 was excluded in the meta-analysis of European studies after quality control filtering (due to MAF<0.05), hence a proxy SNP, rs1246413, in LD with rs12511037 ($r^2$=0.67, D'=1) was tested, whereas insignificant association was observed (P for JMA=0.527; P for interaction=0.176). The meta-regression including study-level characteristics as covariates in the model confirmed the heterogeneity between populations of European and Asian ancestry (GABRR1 SNP rs13215566: P=0.006; PDE10A SNP rs12206610: P=0.0419). For PDE10A, besides ethnicity, average spherical equivalent of each study also explained the inter-study heterogeneity for the interaction effects (P=0.025).

It was further examined whether the underlying assumption of G×E independence held at these three G×E interaction loci. A meta-analysis of logistic regression analysis was performed for education level on AREG rs12511037, GABRR1 rs13215566 and PDE10A rs12296610, adjusting for age, gender and population stratification in the Singapore cohorts (n=9,004). The analysis did not reveal any significant associations between these loci and education level (P≥0.200, $P_{het} \geq 0.118$). Furthermore, the three loci were also not associated with educational attainment in a large meta-analysis of GWAS recently conducted in European cohorts. Thus, the G×E results are unlikely to be biased due to dependence between gene and education.

The association for spherical equivalent in Asian cohorts for four loci identified from European populations was also evaluated. Two of them were replicated (FAM150B: P for JMA=0.013; DIS3L-MAP2K1: P for JMA=0.0042; Table 1). DIS3L-MAP2K1 also showed suggestive SNP×education interaction in Asians (P for interaction=$7.95 \times 10^{-4}$), while this was not significant in Europeans (P for interaction=0.208).

TABLE 2

Three genetic loci associated with spherical equivalent with a significant SNP ×
education interaction in Asian populations, and results in European populations

| SNP (Chr: BP) | Gene | Allele | FREQ | Subgroup | Asians (n = 10,315) β | P | $P_{het}$ | Europeans (n = 40,306) β | P | $P_{het}$ |
|---|---|---|---|---|---|---|---|---|---|---|
| rs12511037 (4: 75334864) | AREG | C/T | 0.91/0.97 | Lower educaiton | 0.07 | 0.243 | | −0.05 | 0.323 | |
| | | | | Higher education | −0.70 | $1.97 \times 10^{-10}$ | | −0.03 | 0.579 | |
| | | | | G × E | −0.89 | $6.87 \times 10^{-11}$ | 0.704 | 0.02 | 0.176 | 0.284 |
| | | | | JMA | | $5.55 \times 10^{-10}$ | 0.405 | | 0.527 | 0.186 |
| rs13215566 (6: 89918638) | GABRR1 | C/G | 0.94/0.84 | Lower educaiton | −0.13 | 0.030 | | −0.03 | 0.258 | |
| | | | | Higher education | −0.68 | $1.46 \times 10^{-8}$ | | −0.01 | 0.817 | |
| | | | | G × E | −0.56 | $8.48 \times 10^{-5}$ | 0.134 | −0.02 | 0.459 | 0.457 |
| | | | | JMA | | $3.81 \times 10^{-8}$ | 0.122 | | 0.502 | 0.630 |
| rs12206610 6: 166016800 | PDE10A | C/T | 0.90/0.87 | Lower educaiton | 0.16 | 0.008 | | 0.01 | 0.759 | |
| | | | | Higher education | −0.59 | $8.16 \times 10^{-8}$ | | 0.01 | 0.810 | |
| | | | | G × E | −0.72 | $2.32 \times 10^{-8}$ | 0.920 | −0.002 | 0.421 | 0.111 |
| | | | | JMA | | $9.21 \times 10^{-9}$ | 0.902 | | 0.954 | 0.305 |

JMA, joint meta-analysis on SNP association and SNP × education on spherical equivalent; the effects estimates presented are derived from the JMA for the lower and higher education group. The effect size and p-value for SNP × education interaction were calculated by the meta-analysis of conducting a 1df Wald test of single interaction parameter (SNP × education). $P_{het}$, p-value for the test of heterogeneity; Allele is listed as risk allele/other allele; FREQ, allele frequency of the risk allele in Asian/European cohorts. SNP rs12511037 was excluded in met-analysis in Europeans because of low MAF (MAF < 0.05). Here we present the results of a proxy SNP rs1246413 (T/G, FREQ for effect allele T = 0.95) in LD with rs12511037 ($r^2$ = 0.67, D' = 1) for Europeans.

Example 4

Joint Meta-Analysis of all Cohorts

Subsequently, a combined meta-analysis was conducted, including both the European and Asian subjects of all 34 studies. This analysis revealed two additional SNPs: ARID2 (P for JMA=$4.38 \times 10^{-8}$) and SLC14A2 (P for JMA=$2.54 \times 10^{-8}$). Both loci showed suggestive association with spherical equivalent in European cohorts, while the association was attenuated in Asian cohorts (Table 1). Genome-wide significant associations were also detected with spherical equivalent for 17 known loci identified in the previous CREAM GWAS.

Example 5

Gene and Education Interactions for GWAS Known Loci

For the previously reported genetic association with spherical equivalent at 39 loci identified from recent two large GWAS, interactions with education were evaluated. Two SNP×education interactions were nominally significant: TJP2 in Europeans (rs11145488; P for interaction=$6.91 \times 10^{-3}$) and SHISA6-DNAH9 in Asians (rs2969180; P for interaction=$4.02 \times 10^{-3}$). In general, the index SNPs tested at 39 loci had larger SNP×education interaction effect on spherical equivalent (meta-regression P for fold changes<0.001). For 20 SNPs with the same direction of the interaction effect, the magnitudes of interaction effects were 4-fold larger on average in Asians than in Europeans (meta-regression P=0.003).

Example 6

Gene Expression in Human Tissues

Using Ocular Tissue Database, the expression of the associated genes was examined in 20 normal human donor eyes. The majority of genes identified were expressed in human retina, sclera or retinal pigment epithelium (RPE) (Table 3). Among these genes, GABRR1 had the highest expression in the retina. The PLIER normalized level of expression of GABRR1 in the retina was 121.7 with an expression value of 21.5 in sclera, suggesting the expression of GABRR1 is more prevalent within the retina. FAM150B was found highly present in the choroid/RPE (expression value of 333.3), while expressed at a much lower level in the retina (29.9). MAP2K1 was widely expressed in the retina, sclera and choroid with expression values greater than 85.7.

TABLE 3

Gene expression of identified loci in human ocular tissues

| GENE | Retina | Sclera | Choroid/RPE |
|---|---|---|---|
| FAM150B | 29.94 | 62.13 | 333.33 |
| PRL | 43.48 | 24.74 | 43.64 |
| FBN1 | 12.88 | 75.26 | 47.08 |
| MAP2K1 | 85.72 | 91.26 | 183.61 |
| DIS3L | 43.20 | 32.95 | 42.16 |
| SLC14A2 | 29.96 | 34.87 | 33.69 |
| AREG | 21.31 | 26.04 | 29.64 |
| GABRR1 | 121.66 | 21.48 | 31.43 |
| PDE10A | 28.19 | 18.87 | 21.46 |

Expression data was obtained from Ocular Tissue Database. The Affymetrix GeneChip Human Exon 1.0 ST (HuEx 1.0) microarrays were used to assess gene expression. Normalization of gene expression was done at both the probe set and metaprobe set level using the Probe Logarithmic Intensity Error (PLIER) method with GC-background correction. The PLIER normalized level of gene expression was presented in the table.

Discussion

The above data represent the most comprehensive genome-wide analysis to date of gene and education interactions in relation to refractive error. Novel genetic loci associated with refractive error were identified by testing the joint contribution of SNP and SNP×education effects in large multi-ethnic populations. Three genes (AREG, GABRR1 and PDE10A) showed strong interactions with education in populations of Asian descent. Apart from confirming known associations with spherical equivalent with 17 previous published loci, using a combined multiracial cohort, 6 novel loci (FAM150B, LINC00340, FBN1, DIS3L-MAP2K1, ARID2 and SLC14A2) significantly associated with spherical equivalent were identified.

Of the novel loci, GABRR1 on chromosome 6q15 (53 kb) is an especially interesting functional candidate suggestive of a role in myopia development. Modulation of synaptic plasticity via GABA-mediated inhibition would be well-placed to alter the "gain" of the visually-guided feedback system controlling refractive development. The lead SNP rs12215566 in GABRR1, together with 7 SNPs within the LD block ($r^2>0.8$), are intronic potentially affecting regulatory motifs (such as zfp128 and gcm1) which may influence transcriptional regulation. As one of the major inhibitory neurotransmitters in the retina, GABA is active in large retinal cells and amacrine cells. It has been reported that antagonists to GABA A, B, and C receptors inhibited form-deprivation myopia in chicks, with greatest effect in the equatorial dimension. GABA receptors also interact with dopamine pathways in the retina. A recent proteomics study has also showed that levels of GABA transporter-1 (GAT-1) are significantly reduced in myopic murine retina after atropine treatment, implying GABA signaling is involved in anti-myopic effects of atropine. Therefore, the present result in humans is in line with animal experiments, supporting the notion that the GABAergic neurotransmitter signaling pathway in the retina could be a potential player in the progression of myopia.

The rs10889855 on chromosome 6 is an intronic variant within the ARID2 gene (AT Rich Interactive Domain 2) and about 500 kb downstream of SNAT1 (Solute Carrier Family 38, Member; Aliases SLC38A1). SNAT1 is a transporter of glutamine, a precursor of GABA. It is also highly expressed in human retina. In previous meta-analysis in CREAM, variants in another glutamate receptor gene GRIA4 (encoding glutamate receptor, ionotropic) were identified; altogether current evidence supports the notion that retinal neurotransmitters GABA and glutamine may be involved in the refractive development.

The strongest association signal for gene and environment interactions was from rs12511037, located 14 kb downstream the AREG gene (amphiregulin). AREG is a ligand of the epidermal growth factor receptor (EGFR) promoting the growth of normal epithelial cells, which is critical for cell differentiation and proliferation such as regrowth of the wounded cornea. A link has been found between the muscarinic acetylcholine receptors and the EGFR, as EGFR controls fluid secretion in muscarinic system.

Another novel association, rs16949788 on chromosome 15, derives from a region that spans DIS3L and MAP2K1. MAP2K1 encodes mitogen-activated protein kinase 1 which binds to muscarinic receptors during proliferation and inhibits the proliferation of human scleral fibroblasts exposed to all-trans retinoic acid. The muscarinic antagonist atropine inhibits the development of myopia in animal models and human intervention studies. All-trans retinoic acid is a modulator of ocular growth, inhibiting the proliferation of human scleral fibroblasts.

FBN1 (Fibrillin 1) encodes a large extracellular matrix glycoprotein, a member of the fibrillin family. Mutations in FBN1 cause Marfan's syndrome, a disorder of connective tissue affecting the ocular, skeletal and cardiovascular systems. As a candidate gene for myopia, attempts to study its association with myopia previously produced inconclusive results, probably due, in part, to underpowered studies with insufficient sample sizes. Using data from a large multi-ethnic population, the present results support the role of FBN1 in myopia development.

The genome-wide significant SNPs for the JMA did not exhibit any interactions with education in Europeans, in contrast to the significant interactive effect among Asians. In particular, the interactions of AREG, GABRR1 and PDE10A with education were evident in Asian populations only, but not in Europeans. There are a number of possible reasons. First, the observed heterogeneity may reflect the intense education systems in Asia. The higher education level was associated with myopic shift at an average of a 1.16 D in refraction in Asians, but with only a 0.56 D in Europeans. It is possible that the gene and education interplay may manifest more in such a condition with the strong education effects, as genetic effects are generally modest across the populations. Second, the population distribution of refractive error is more myopic in Asians (−0.60 D versus 0.10 D in Europeans). A high prevalence of myopia is likely to associate with other unmeasured lifestyle exposures, which were not accounted for in the current study. Third, education systems varied widely across studies. We chose to divide education levels into two categories but this cut-off may not reflect the same education intensity or true underlying risk for myopia across Europeans and Asians. Any misclassification in environment measurements may bias the effect towards or away from the null. Last, education in adults may not be an accurate surrogate for cumulative near work activity. The level of education attained may be a crude marker of reading intensity and computer use during the crucial years prior to the onset of myopia. These factors, accompanying with varying allele frequencies at the associated SNPs, might obscure the power to detect the interaction effects in individuals of European ancestry. Whether such G×E interaction is ancestry-specific warrants further evaluation.

Education level reflects the accumulated effect of near work, such as reading and writing. It was thus examined whether there was evidence for SNP×near work interactions associated with spherical equivalent at the three newly-identified loci (AREG, GABRR1 and PDE10A) in cohorts of children of Asian and European ancestry (combined n=5,835). Tentative support for a SNP×near work interaction was observed for PDE10A SNP rs12206610 (P for interaction=0.032; $P_{het}$=0.927). Weaker support for an interaction was noted at GABRR1 SNP rs13215566 (P for interaction=0.109; $P_{het}$=0.118) and at the AREG SNP rs12511037 (P for interaction=0.80, $P_{het}$=0.224), although the direction of interaction effect was largely consistent across pediatric studies with that observed in adults. A lack of strong SNP×near work associations at these loci leaves open the possibility that environmental risk exposures other than near work might underlie the SNP×education interaction seen in the adult Asian samples.

In summary, 9 novel loci associated with refractive error were identified in a large multi-ethnic cohort study by a joint meta-analysis approach. The present data provide evidence that specific genetic variants interact with education to influence refractive development, and further support a role for GABA neurotransmitter signaling in myopia development. These findings provide promising candidate genes for follow-up work and may lead to new genetic targets for therapeutic interventions on myopia.

The invention claimed is:

1. A method for the therapeutic treatment of myopia in a human subject having myopia, comprising administering to the human subject a therapeutically effective amount of an agent that decreases epidermal growth factor receptor (EGFR) signaling in the subject so as to treat the myopia in the subject, wherein said agent is selected from the group consisting of:

an isolated antibody, antibody fragment or antibody mimetic directed against EGFR in a blocking manner in said subject; wherein said agent binds to human EGFR and wherein said agent is administered intraocularly, including intravitreally.

2. The method of claim 1, wherein said antibody fragment is selected from the group consisting of Fab fragments, F(ab')$_2$ fragments and Fab' fragments.

3. The method of claim 1, wherein said antibody mimetic is selected from the group consisting of a single-chain variable fragment (scFv), a single-domain antibody, a DARPin, and a peptide aptamer.

* * * * *